(12) United States Patent
Unalmis

(10) Patent No.: US 11,692,858 B2
(45) Date of Patent: Jul. 4, 2023

(54) FLOW RATE OPTIMIZER

(71) Applicant: Weatherford Technology Holdings, LLC, Houston, TX (US)

(72) Inventor: Omer Haldun Unalmis, Kingwood, TX (US)

(73) Assignee: Weatherford Technology Holdings, LLC, Houston, TX (US)

( * ) Notice: Subject to any disclaimer, the term of this patent is extended or adjusted under 35 U.S.C. 154(b) by 268 days.

(21) Appl. No.: 16/894,482

(22) Filed: Jun. 5, 2020

(65) Prior Publication Data
US 2021/0381867 A1 Dec. 9, 2021

(51) Int. Cl.
| | |
|---|---|
| G01F 1/66 | (2022.01) |
| E21B 47/113 | (2012.01) |
| E21B 47/107 | (2012.01) |
| G01F 1/74 | (2006.01) |
| G01N 33/28 | (2006.01) |

(52) U.S. Cl.
CPC ............ *G01F 1/666* (2013.01); *E21B 47/107* (2020.05); *E21B 47/114* (2020.05); *G01F 1/74* (2013.01); *G01N 33/2823* (2013.01)

(58) Field of Classification Search
CPC .......... G01F 1/666; G01F 1/74; E21B 47/114; E21B 47/107; G01N 33/2823
USPC .................................................... 166/250.01
See application file for complete search history.

(56) References Cited

U.S. PATENT DOCUMENTS

| | | | |
|---|---|---|---|
| 6,945,095 B2 | 9/2005 | Johansen | |
| 7,526,966 B2 | 5/2009 | Gysling et al. | |
| 7,571,633 B2 | 8/2009 | Gysling et al. | |
| 8,641,813 B2 | 2/2014 | Gysling | |
| 9,383,476 B2 | 7/2016 | Trehan et al. | |
| 2014/0076547 A1* | 3/2014 | Unalmis | E21B 47/06 166/250.01 |

FOREIGN PATENT DOCUMENTS

WO 2011020017 A3 5/2011

OTHER PUBLICATIONS

Ahmed Yasin Abukhamsin, "Inflow Profiling and Production Optimization in Smart Wells Using Distributed Acoustic and Temperature Measurements," Jun. 2017, 193 Pgs.

(Continued)

*Primary Examiner* — John Fitzgerald
*Assistant Examiner* — Rodney T Frank
(74) *Attorney, Agent, or Firm* — Cabello Hall Zinda, PLLC

(57) ABSTRACT

Methods and apparatus for hydrocarbon monitoring are provided. A method that may be performed by a flowmeter or monitoring system includes receiving downhole measurements of a flowing fluid from a flowmeter; determining a standard phase fraction of the flowing fluid based on the downhole measurements from the flowmeter; receiving surface measurements of the flowing fluid; determining a surface phase fraction of the flowing fluid based on the surface measurements; comparing the standard phase fraction to the surface phase fraction; based on the comparison being greater than a predetermined threshold, using the surface measurements as a reference to adjust a speed of sound (SoS) of a first phase until a target value is achieved; and receiving additional downhole measurements of the flowing fluid from the flowmeter, wherein the flowmeter is operating using the adjusted SoS of the first phase.

30 Claims, 7 Drawing Sheets

(56) References Cited

OTHER PUBLICATIONS

Ö. H. Ünalmis, "Subsea Multiphase Flow Measurement—a New Approach," 30th International North Sea Flow Measurement Workshop, Oct. 23-26, 2012, pp. 1-16.

Haldun, U. O., "Sound Speed in Downhole Flow Measurement," The Journal of the Acoustic Society of America, vol. 140, No. 1, Jul. 19, 2016, 12-pgs.

Int'l Search Report and Written Opinion in counterpart PCT Appl. PCT/US2021/022398, dated Jun. 23, 2021, 12-pgs.

\* cited by examiner

FLOW RATE OPTIMIZER

BACKGROUND

Field of the Invention

Aspects of the present disclosure generally relate to hydrocarbon production and, more particularly, to deriving phase component fractions and determining phase flow rates for a fluid mixture flowing in a conduit.

Description of the Related Art

In the petroleum industry, as in many other industries, ability to monitor flow of fluids in process pipes in real-time offers considerable value. Oil and gas operators measure individual oil, water, and/or gas flow rates within an overall production flow stream containing a mixture of these three phase components. This information may be used to improve and optimize well production, allocate royalties, prevent corrosion based on the amount of water, and determine the well performance.

Production from gas wells may also include a significant liquid content (water, hydrocarbon oil, condensate, or combinations thereof). Flows with relatively high gas amounts with respect to liquid amounts (e.g., around or below 5% liquid by volume) are described as wet-gas flows and represent the high gas-volume-fraction (GVF) end of multiphase flows. Various prior flowmeters attempt to enable flow rate measurements or determinations of the phase components of these high-GVF flows using methodologies that are complex and difficult to implement, yet still yield results with less than desired accuracy.

SUMMARY

Certain aspects of the present disclosure provide a method for hydrocarbon monitoring. The method generally includes receiving downhole measurements of a flowing fluid from a flowmeter; determining a standard phase fraction of the flowing fluid based on the downhole measurements from the flowmeter; receiving surface measurements of the flowing fluid; determining a surface phase fraction of the flowing fluid based on the surface measurements; comparing the standard phase fraction to the surface phase fraction; based on the comparison being greater than a predetermined threshold, using the surface measurements as a reference to adjust a speed of sound (SoS) of a first phase until a target value is achieved; and receiving additional downhole measurements of the flowing fluid from the flowmeter, wherein the flowmeter is operating using the adjusted SoS of the first phase.

According to certain aspects, the method further includes determining at least one of an updated in-situ phase fraction, an updated standard phase fraction, or updated phase flow rates of the flowing fluid, based on the additional downhole measurements.

According to certain aspects, the standard phase fraction comprises a water-in-liquid ratio (WLR) at standard conditions.

According to certain aspects, the surface measurements of the flowing fluid are received from at least one of a wellhead or a separator.

According to certain aspects, the target value includes a target mixture SoS. For some aspects, using the surface measurements as the reference to adjust the SoS of the first phase includes: calculating a target mixture density based on the surface phase fraction; calculating the target mixture SoS based on the target mixture density and the downhole measurements; and changing the SoS of the first phase until a resulting mixture SoS obtained from the Wood's equation is within a predetermined deviation from the target mixture SoS, while leaving a SoS of a second phase constant. For other aspects, the SoS of the first phase is a SoS of oil and the SoS of the second phase is a SoS of water. For still other aspects, the SoS of the first phase is a SoS of gases in the fluid, the SoS of the second phase is a SoS of liquids in the fluid, and the phase fraction comprises a liquid volume fraction (HL) of the fluid. For still other aspects, calculating the target mixture density includes: predicting an in-situ phase fraction based on the surface phase fraction, the standard phase fraction, a downhole pressure measurement, a downhole temperature measurement, a surface pressure measurement, a surface temperature measurement, a standard pressure, and a standard temperature; and calculating the target mixture density based on the in-situ phase fraction. For still other aspects, calculating the target mixture SoS is based on the Korteweg-Lamb equation.

According to certain aspects, the method further includes updating a parameter file for the flowmeter with the adjusted SoS of the first phase. For some aspects, the adjusted SoS of the first phase is at a measured downhole temperature and a measured downhole pressure and the updating includes: extrapolating additional adjusted speeds of sound of the first phase for temperatures other than the measured downhole temperature and for pressures other than the measured downhole pressure; and writing the adjusted SoS of the first phase at the measured downhole temperature and pressure and the extrapolated additional adjusted speeds of sound of the first phase to the parameter file for the flowmeter.

According to certain aspects, the method further includes applying a conversion factor to at least one of the standard phase fraction or the surface phase fraction before the comparing.

According to certain aspects, the flowmeter is an optical flowmeter.

According to certain aspects, the method further includes: determining an updated standard phase fraction of the flowing fluid based on the additional downhole measurements; receiving additional surface measurements of the flowing fluid; determining an updated surface phase fraction of the flowing fluid based on the additional surface measurements; comparing the updated standard phase fraction to the updated surface phase fraction; based on the comparison of the updated standard and surface phase fractions being greater than the predetermined threshold, using the additional surface measurements as an updated reference to alter the SoS of the first phase until an updated target value is achieved; and receiving further downhole measurements of the flowing fluid from the flowmeter, wherein the flowmeter is operating using the altered SoS of the first phase. For some such aspects, the method further includes calculating adjustments to past downhole measurements based on the altered SoS of the first phase.

According to certain aspects, the method further includes: calculating adjustments to past downhole measurements based on the adjusted SoS of the first phase.

Certain aspects of the present disclosure provide a processing system for hydrocarbon monitoring. The processing system is configured to receive downhole measurements of a flowing fluid from a flowmeter; to receive downhole measurements of a flowing fluid from a flowmeter; to receive surface measurements of the flowing fluid; to determine a surface phase fraction of the flowing fluid based on the surface measurements; to compare the standard phase fraction to the surface phase fraction; to use the surface measurements as a reference to adjust a SoS of a first phase until a target value is achieved, based on the comparison being greater than a predetermined threshold; and to receive additional downhole measurements of the flowing fluid from the flowmeter, the flowmeter being configured to operate using the adjusted SoS of the first phase.

Certain aspects of the present disclosure provide a computer-readable medium (e.g., a computer-readable storage device) for hydrocarbon monitoring. The computer-readable medium generally includes instructions which, when executed by a processing system, cause the processing system to perform operations including receiving downhole measurements of a flowing fluid from a flowmeter; determining a standard phase fraction of the flowing fluid based on the downhole measurements from the flowmeter; receiving surface measurements of the flowing fluid; determining a surface phase fraction of the flowing fluid based on the surface measurements; comparing the standard phase fraction to the surface phase fraction; based on the comparison being greater than a predetermined threshold, using the surface measurements as a reference to adjust a SoS of a first phase until a target value is achieved; and receiving additional downhole measurements of the flowing fluid from the flowmeter, wherein the flowmeter is operating using the adjusted SoS of the first phase.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only typical aspects of this disclosure and are therefore not to be considered limiting of its scope, for the disclosure may admit to other equally effective aspects.

DETAILED DESCRIPTION

Certain aspects of the present disclosure provide techniques and apparatus for monitoring hydrocarbons by deriving downhole phase fractions and determining downhole flow rates for individual phases of a multiphase flow. The techniques and apparatus derive downhole phase fractions and flow rates based on several parameters: downhole pressure ($P_d$), downhole temperature ($T_d$), speed of sound (SoS) of the mixture, a downhole flow velocity of the mixture, well test pressure ($P_{WT}$), well test temperature ($T_{WT}$), and a surface phase fraction of the mixture. The described parameters may be directly measured and used to derive downhole phase fractions and single-phase parameters. The single-phase parameters may be used to update a parameter file for a flowmeter to improve accuracy of the flowmeter in measuring parameters of the flow in the well.

The techniques and apparatus for deriving downhole phase fractions and determining downhole flow rates may be based on measuring parameters of the fluid downhole, determining an initial phase fraction, measuring parameters of the fluid at the surface, calculating an updated phase fraction, and updating a parameter file used with the flowmeter based on differences between the initial phase fraction and the updated phase fraction.

Previously known downhole flowmeters typically consist of Venturi-type devices, which are typically suitable for single-phase flows and have limited flow rate ranges due to their low turndown ratios (i.e., ratio of maximum flow rate to minimum flow rate). Because these devices measure single-phase flows, such devices do not provide important measurements, such as water cut on the surface, that typically involve measurements of two-phase flow rates.

Some technologies involving distributed acoustic sensing (DAS) may be used for downhole monitoring. A DAS system is typically capable of measuring SoS and, depending on its installation/configuration and the type of application, a DAS system may also be capable of measuring flow velocity. However, the data acquired in a DAS system for the complete length of fiber usually adds up to extremely large amounts, and thus, a selective process and reduction of data are desirable. In the current state of DAS technology, the data is usually post-processed and not reported in real-time.

One technique for improving performance of a flowmeter is to obtain the correct SoS of the single-phase fluids in the mixture. In most cases, this is a difficult process and involves analysis of bottomhole fluid samples in a laboratory using reliable SoS measuring techniques. This difficult and typically expensive process consumes resources and time. In some cases, the laboratory-measured single-phase SoS is not a good representation of the actual SoS. In some cases, satisfactory single-phase speeds of sound are not obtained from the laboratory, due to laboratory-related issues.

Figure 1:
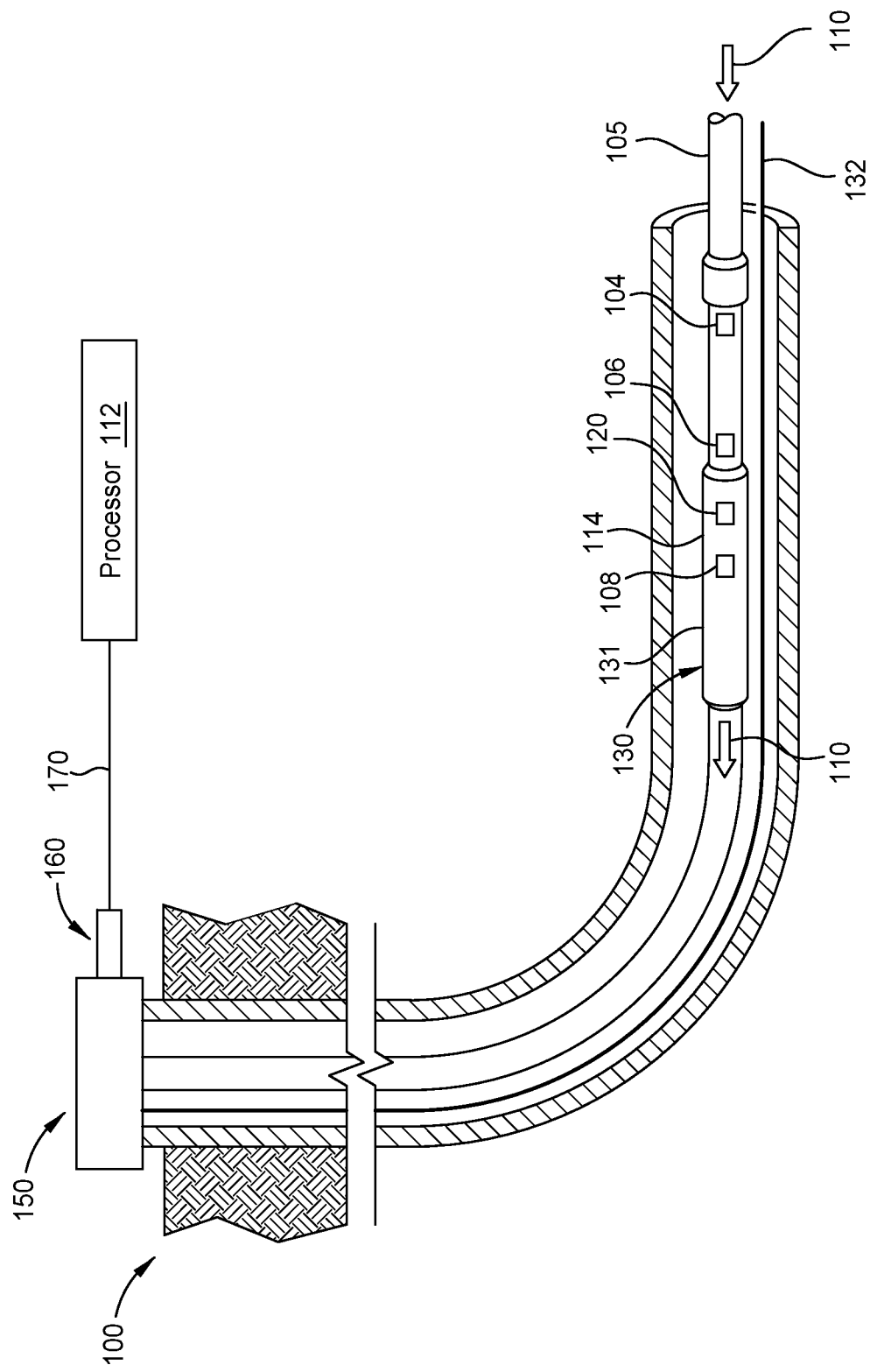
FIG. 1 illustrates an example system that may be utilized to perform multiphase flow rate measurements, according to aspects of the present disclosure.

FIG. 1 illustrates an example system 100 that may be utilized to perform multiphase flow rate measurements of a fluid mixture flow 110 (i.e., a fluid flow) in a conduit 105 in accordance with aspects of the present disclosure. For example, the conduit 105 may be production tubing disposed in a wellbore.

As illustrated, the example system 100 includes a flowmeter 130 that includes at least one pressure sensor 108 (e.g., a static pressure sensor) and at least one temperature sensor 120 in one section 131 for measuring pressure at a point 114 and temperature of the fluid mixture within conduit 105. The pressure sensor may be any suitable type of sensor that measures pressure directly, such as a diaphragm configured to flex and apply a force to an optical fiber within the flowmeter 130. The system 100 also includes one or more temperature sensors 120, which may measure the mixture temperature at or near the same point 114 at which pressure is sensed by the pressure sensor 108. Pressure and temperature readings taken from the sensors may be used to quantify the component density and viscosity of the oil, water, and gas phases of the fluid mixture. The component density and viscosity of oil, water, and gas phases may then be used in an iterative algorithm which is explained in more detail below.

The flowmeter 130 may be an optical flowmeter or an electrical flowmeter. While illustrated with a flowmeter 130, the example system 100 is not so limited, and may include a sound measurement system (electronic or optical) for determining a fluid flow rate, such as a distributed acoustic sensing (DAS) system, which may include an optical waveguide 132.

The derivation process uses a flowmeter's initial downhole and standard measurements, as explained in detail below. The downhole phase fraction is derived based on a surface phase fraction (e.g., as determined by a well test or separator test), initial downhole and phase fraction measurements by the flowmeter, and the pressure measurements at the locations of flowmeter, test separator, as well as the standard conditions. The process involves a first-order interpolation of the phase fractions along the pressure interval. An example of the parameters involved in the interpolation process are shown in Table 1:

TABLE 1

Interpolation parameters

| | Locations and expected relationships | | | | |
|---|---|---|---|---|---|
| Parameter | Downhole | Relationship | Separator | Relationship | Standard |
| Pressure (P) | $P_d \approx 100$ bar | > | $P_{sep} \approx 10$ bar | > | $P_{std} \approx 1$ bar |
| Local phase fraction ($\phi$) | $\phi_d$ | ? | $\phi_{sep}$ | ? | $\phi_{std}$ |
| Inverse water-in-liquid ratio $(WLR)^{-1}$ | $(WLR_d)^{-1}$ | > | $(WLR_{sep})^{-1}$ | > | $(WLR_{std})^{-1}$ |
| Liquid volume fraction (HL) | $HL_d$ | > | $HL_{sep}$ | > | $HL_{std}$ |

The system 100 may also include a fluid bulk velocity sensor 106 and a SoS meter 104 that allows measurement of SoS of the fluid mixture. In some cases, the SoS meter 104, the bulk velocity sensor 106, or both measurement devices may include a pressure sensor array.

An example of such a SoS meter 104 may include two or more sensing elements that form an array. Spacing between the sensing elements may enable sensing acoustic signals traveling at the SoS through the fluid flow 110 within the conduit 105 (referred to as "acoustic sensing") and can also enable sensing short duration local pressure variations traveling with the fluid flow (referred to as "flow velocity sensing"). The acoustic signals and/or the local pressure variations commonly originate from naturally occurring phenomena. For some aspects, the sensor elements may be formed with optical fiber in the flowmeter 130 within the conduit 105. Other pressure-measuring devices, such as piezoelectric- or polyvinylidene fluoride (PVDF)-based detectors, may also be used.

The system 100 may also include one or more sensors (e.g., pressure and/or temperature sensors) at a wellhead 150 or separator 160 of the well.

A processor 112 may receive signals conveying measurements from the flowmeter 130 and/or sensors at the wellhead 150 or separator 160 via one or more cables 170. The cables 170 may, for example, include optical waveguides and/or electric wires.

Example Techniques for Deriving Downhole Phase Component Fractions and Determining Downhole Flow Rates Aspects of the present disclosure use surface well test data to derive a target downhole phase fraction (e.g., water cut).

According to aspects of the present disclosure, the pressure interval is selected for the interpolation process based on pressure being the main driving mechanism for the fluid to move from a reservoir to the surface, and because pressure is a dominant factor on the fluid behavior, particularly oil. Unlike water, oil (in the mixture in a well) is a compressible fluid and may contain dissolved gas at high pressures. As the oil moves from the reservoir (a high-pressure environment) to the surface (a low-pressure environment), gas dissolved in the oil effervesces (i.e., is released) from the oil phase. As a result, the oil flow rate from the well decreases, and the WLR (water-in-liquid ratio) of the flowing mixture increases, as the mixture moves toward the surface (i.e., in the opposite direction from the pressure variation). Thus interpolating the inverse of WLR along the pressure interval may be sufficiently accurate for well operation purposes. HL (liquid volume fraction) also decreases as the fluid mixture moves to the surface (i.e., in the same direction as the pressure variation). Expressions for WLR and HL, and the relation between HL and GVF (gas volume fraction) are given below:

$$WLR = \frac{Q_{water}}{Q_{water} + Q_{oil}} \quad (1)$$

$$HL = \frac{Q_{water} + Q_{oil}}{Q_{gas} + Q_{water} + Q_{oil}} = 1 - \frac{Q_{gas}}{Q_{gas} + Q_{water} + Q_{oil}} = 1 - GVF \quad (2)$$

where Q represents the volumetric flow rate.

In aspects of the present disclosure, when the phase fraction to be derived is the WLR, an initial derivation for the in-situ $WLR_d$ can be obtained using the above-described interpolation (i.e., interpolation on the pressure interval) in the following manner:

$$\frac{(WLR_d)^{-1} - (WLR_{sep})^{-1}}{(WLR_d)^{-1} - (WLR_{std})^{-1}} = \left(\frac{P_d - P_{sep}}{P_d - P_{std}}\right) = A \quad (3)$$

where A represents the pressure ratio.

$$\frac{WLR_d}{WLR_{sep}} = 1 - \left(1 - \frac{WLR_d}{WLR_{std}}\right)A \quad (4)$$

$$WLR_d = WLR_{sep}\left\{1 - \left(1 - \frac{WLR_d}{WLR_{std}}\right)A\right\} \quad (5)$$

Equation 5 can be used to derive the in-situ phase fraction (i.e., the phase fraction of interest). All of the terms in the right-hand side are known including the ratio of the $WLR_d/WLR_{std}$, which is directly obtained from the existing flowmeter data, and the variation of that ratio is not expected to change.

In aspects of the present disclosure, when the phase fraction to be derived is the HL, an initial derivation for the in-situ $HL_d$ can be obtained using the above-described interpolation (i.e., interpolation on the pressure interval) in the following manner:

$$\frac{HL_d - HL_{sep}}{HL_d - HL_{std}} = \left(\frac{P_d - P_{sep}}{P_d - P_{std}}\right) = A \quad (6)$$

Solving for $HL_d$, $$HL_d = \frac{HL_{sep}}{1-A} - \frac{A}{1-A}(HL_{std}) \quad (7)$$

Equation 7 can be used to derive the in-situ phase fraction (i.e., the phase fraction of interest). All the terms in the right-hand side are known from the separator and initial flowmeter measurements.

Once the target phase fraction is determined, the mixture density at the meter location can be calculated as shown below:

$$\rho_{mix} = (1-\phi_d)\rho_1 + \phi_d\rho_2 \quad (8)$$

where
- $\rho_{mix}$: mixture density downhole at downhole pressure (P) and temperature (T)
- $\rho_1$: density of phase 1 of the mixture at downhole P and T
- $\rho_2$: density of phase 2 of the mixture at downhole P and T
- $\phi_d$: derived target phase fraction {e.g., WLR (water-in-liquid ratio) or GVF (gas volume fraction), or HL}

In aspects of the present disclosure, the corresponding target mixture SoS may be backward calculated using the Korteweg-Lamb equation, as shown below in Equation 9:

$$SoS_{pipe} = \left\{\frac{1}{SoS_{mix}^2} + \rho_{mix}\left(\frac{d}{t}\right)\left(\frac{1-v^2}{E}\right)\right\}^{-1/2} \quad (9)$$

where
- $SoS_{pipe}$: speed of sound of medium in the pipe measured by the flowmeter
- $SoS_{mix}$: speed of sound of mixture in the infinite medium
- d: pipe diameter
- t: pipe wall thickness
- E: modulus of elasticity of pipe material
- v: Poisson ratio of pipe material (~0.3 for rigid bodies such as steel)

In aspects of the present disclosure, once the target mixture density and the target mixture SoS are determined, the single-phase SoS of the stable phase (e.g., water) may be held as a constant while the single-phase SoS of the unstable phase (e.g., oil) is systematically changed until the mixture SoS obtained from the Wood's equation (see Equation 10, below) is equal to the target mixture SoS determined in Equation 9.

$$SoS_{mix} = \left\{[(1-\phi_d)\rho_1 + \phi_d\rho_2]\left[\frac{1-\phi_d}{\rho_1 a_1^2} + \frac{\phi_d}{\rho_2 a_2^2}\right]\right\}^{-1/2} \quad (10)$$

where
- $SoS_{mix}$: speed of sound of mixture in the infinite medium
- $a_1$: SoS of phase 1 at downhole P and T
- $a_2$: SoS of phase 2 at downhole P and T
- $\rho_1$: density of phase 1 of the mixture at downhole P and T
- $\rho_2$: density of phase 2 of the mixture at downhole P and T
- $\phi_d$: local phase fraction measured by flowmeter downhole In aspects of the present disclosure, the single-phase SoS value of the unstable phase that satisfies Equation 10 at the measured pressure (P) and temperature (T) is updated in a parameter file that is used for calculation of phase flow rates. Similarly, a proportional change in single-phase SoS is extrapolated for other pressure and temperature (P/T) grid points of the parameter file. Next, the standard flow rates and phase fractions are forward calculated using the flow algorithm of the flowmeter, and the match between the well test results and the flowmeter results is verified. Once the match is achieved, the flowmeter may continue to provide correct phase fractions and flow rates in the absence of well tests.

The above passages describe how to derive or predict the inline target phase fraction when the surface phase fraction is available. Because phase fraction, density, and SoS are all coupled, the external information may be utilized in the equations above to solve for other unknowns in a backward calculation mode using Equations 8 and 9 to determine the target $\rho_{mix}$ and the target $\phi_d$, respectively. In the absence of surface information, a backward calculation starting from Equation 8 is not possible, since there are two unknowns: $\rho_{mix}$ and $\phi_d$.

According to aspects of the present disclosure, $\rho_{mix}$ and $\phi_d$ may be calculated, and flow measurements may be made, in the steady-state operation of a flowmeter (e.g., flowmeter 130). In aspects of the present disclosure, a solution may be reached by a forward calculation of the coupled quantities. When the external information is available and once the SoS table (included in a parameter table for the flowmeter) of the unstable phase is optimized (that is, updated to incorporate adjustments based on measurements of the well), the flowmeter algorithm described herein may be used in an ongoing manner to determine unknown quantities in a forward calculation mode. The forward calculation mode makes use of the available information provided in the parameter file, which includes (nonoptimized or optimized) tables of SoS and tables of other fluid properties, such as density and viscosity, of the individual phases.

In aspects of the present disclosure, fluid compressibility has the following relation with density and SoS:

$$\kappa = \frac{1}{\rho a^2} \quad (11)$$

where
ρ: the fluid density,
a: the SoS in infinite fluid medium, and
κ: the fluid compressibility.

When dealing with multiphase flows, a typical approach is to use a volumetric proportion approach to calculate the mixture compressibility. For example, in a two-phase well-mixed flow of oil and water, the compressibility of the mixture can be written as $$\kappa_{mix} = \phi_o \kappa_o + \phi_w \kappa_w \quad (12)$$

where
φ: the phase fraction, with the indices "mix, o, w" referring to mixture, oil, and water, respectively.

Using Equation 11 in Equation 12 and recognizing that in an oil-and-water mixture, $\phi_o = 1 - WLR$ and $\phi_w = WLR$, results in:

$$\frac{1}{\rho_{mix} a_{mix}^2} = \frac{(1 - WLR)}{\rho_o a_o^2} + \frac{WLR}{\rho_w a_w^2} \quad (13)$$

The SoS values in the above expression ($a_{mix}$ or $SoS_{mix}$, $a_o$, and $a_w$) all refer to the SoS in the infinite medium of the mixture, oil, and water, respectively. It may be noted that Equation 13 is the Wood's equation (Equation 10) written in a slightly different form. At this point, Equation 13 has three unknowns: $\mu_{mix}$ and $a_{mix}$ (=$SoS_{mix}$) on the left side of the equation and WLR on the right side of the equation. In aspects of the present disclosure, $\rho_{mix}$ and $SoS_{mix}$ may be written in terms of WLR to change Equation 13 to an equation with one unknown. This may be achieved in the following manner: $\rho_{mix}$ can be written directly in terms of WLR using Equation 8, above. For the mixture SoS, the Korteweg-Lamb equation (Equation 9) may be used to write $SoS_{mix}$ in terms of $SoS_{pipe}$, which is measured by the flowmeter, and $\rho_{mix}$, which can be rewritten in terms of WLR using Equation 8. Thus, the left side of Equation 13 becomes:

$$\frac{1}{\rho_{mix} SoS_{mix}^2} = \frac{1}{\{(1-WLR)\rho_0 + (WLR)\rho_w\} SoS_{pipe}^2} - \left(\frac{d}{t}\right)\left(\frac{1-v^2}{E}\right) \quad (14)$$

Equation 14 may be used in the left side of Equation 13 to derive a single-equation system with a single unknown, with the unknown being the WLR, as shown below:

$$\frac{1}{\{(1-WLR)\rho_0 + (WLR)\rho_w\} SoS_{pipe}^2} - \left(\frac{d}{t}\right)\left(\frac{1-v^2}{E}\right) = \frac{(1-WLR)}{\rho_o a_o^2} + \frac{WLR}{\rho_w a_w^2} \quad (15)$$

In aspects of the present disclosure, Equation 15 can be rearranged to become a second-degree polynomial with WLR as the variable. The steps of this rearrangement are:

$$\left\{\frac{(1-WLR)}{\rho_o a_o^2} + \frac{WLR}{\rho_w a_w^2} + \left(\frac{d}{t}\right)\left(\frac{1-v^2}{E}\right)\right\} SoS_{pipe}^2 = \frac{1}{\{(1-WLR)\rho_0 + (WLR)\rho_w\}}$$

$$\left\{\frac{SoS_{pipe}^2(1-WLR)}{\rho_o a_o^2} + \frac{SoS_{pipe}^2 WLR}{\rho_w a_w^2} + SoS_{pipe}^2\left(\frac{d}{t}\right)\left(\frac{1-v^2}{E}\right)\right\} =$$

$$\frac{1}{\{(1-WLR)\rho_0 + (WLR)\rho_w\}}$$

$$\left\{\frac{SoS_{pipe}^2(1-WLR)}{\rho_o a_o^2} + \frac{SoS_{pipe}^2 WLR}{\rho_w a_w^2} + SoS_{pipe}^2\left(\frac{d}{t}\right)\left(\frac{1-v^2}{E}\right)\right\}$$

$$\{(1-WLR)\rho_0 + (WLR)\rho_w\} - 1 = 0$$

$$\left\{SoS_{pipe}^2\left(\frac{1}{\rho_w a_w^2} - \frac{1}{\rho_o a_o^2}\right) WLR + SoS_{pipe}^2\left[\left(\frac{d}{t}\right)\left(\frac{1-v^2}{E}\right) + \frac{1}{\rho_o a_o^2}\right]\right\}$$

$$\{(\rho_w - \rho_0)WLR + \rho_0\} - 1 = 0$$

Substituting $$SoS_{pipe}^2\left(\frac{1}{\rho_w a_w^2} - \frac{1}{\rho_o a_o^2}\right) WLR = A,$$

$$SoS_{pipe}^2\left[\left(\frac{d}{t}\right)\left(\frac{1-v^2}{E}\right) + \frac{1}{\rho_o a_o^2}\right] = B,$$

$$(\rho_w - \rho_o) = C, \text{ and}$$

$$\rho_o = D \text{ yields:}$$

$$(A \cdot WLR + B)(C \cdot WLR + D) - 1 = 0$$

$$A \cdot C \cdot WLR^2 + (A \cdot D + B \cdot C) \cdot WLR + B \cdot D - 1 = 0$$

$$WLR^2 + \left(\frac{A \cdot D + B \cdot C}{A \cdot C}\right) WLR + \left(\frac{B \cdot D - 1}{A \cdot C}\right) = 0.$$

Substituting $$\left(\frac{A \cdot D + B \cdot C}{A \cdot C}\right) = \beta \text{ and}$$

$$\left(\frac{B \cdot D - 1}{A \cdot C}\right) = \lambda \text{ yields:}$$

$$WLR^2 + \beta \cdot WLR + \lambda = 0$$

$$WLR_{1,2} = \frac{-\beta \pm \sqrt{\beta^2 - 4\lambda}}{2}.$$

Substituting $$\beta^2 - 4\lambda = \delta \text{ yields:}$$

$$WLR_{1,2} = \frac{-\beta \pm \sqrt{\delta}}{2} \quad (16)$$

where:

$$\beta = \frac{A \cdot D + B \cdot C}{A \cdot C},$$

$$\lambda = \frac{B \cdot D - 1}{A \cdot C},$$

$$\delta = \beta^2 - 4\lambda,$$

$$A = SoS_{pipe}^2\left(\frac{1}{\rho_w a_w^2} - \frac{1}{\rho_o a_o^2}\right),$$

$$B = SoS_{pipe}^2\left[\left(\frac{d}{t}\right)\left(\frac{1-v^2}{E}\right) + \frac{1}{\rho_o a_o^2}\right],$$

$$C = (\rho_w - \rho_0), \text{ and}$$

$$D = \rho_0$$

According to aspects of the present disclosure, in a typical oil-and-water mixture, the valid root of Equation 16 is always the positive root. This can be seen from the uniquely changing well-behaved curve (e.g., curve 202 in FIG. 2) along which each SoS value corresponds to a unique WLR. However, this may not be true in a gas-and-liquid mixture (see [0053] below). Once the inline phase fraction WLR is determined, the inline phase flow rates can be calculated as follows:

$$Q_{total} = V \cdot \text{Area}$$

$$Q_{oil} = Q_{total} \cdot (1 - WLR)$$

$$Q_{water} = Q_{total} \cdot WLR \quad (17)$$

In aspects of the present disclosure, a forward calculation procedure for a gas-and-liquid solution may be similar to the above-described procedure for the oil-and-water mixture. The procedure can be repeated for a two-phase well-mixed flow of gas and liquid, as shown below:

$$\kappa_{mix} = \phi_g \kappa_g + \phi_L \kappa_L \quad (18)$$

$$\frac{1}{\rho_{mix} a_{mix}^2} = \frac{(1-HL)}{\rho_g a_g^2} + \frac{HL}{\rho_L a_L^2} \quad (19)$$

$$\frac{1}{\rho_{mix} SoS_{mix}^2} = \frac{1}{\{(1-HL)\rho_g + (HL)\rho_L\} SoS_{pipe}^2} - \left(\frac{d}{t}\right)\left(\frac{1-v^2}{E}\right) \quad (20)$$

$$\frac{1}{\{(1-HL)\rho_g + (HL)\rho_L\} SoS_{pipe}^2} - \left(\frac{d}{t}\right)\left(\frac{1-v^2}{E}\right) = \frac{(1-HL)}{\rho_g a_g^2} + \frac{HL}{\rho_L a_L^2} \quad (21)$$

$$HL_{1,2} = \frac{-\beta^* \pm \sqrt{\beta^{*2} - 4\lambda^*}}{2} \quad (22)$$

$$HL_{1,2} = \frac{-\beta^* \pm \sqrt{\delta^*}}{2}$$

where $$\beta^* = \frac{A^* \cdot D + B^* \cdot C^*}{A^* \cdot C^*},$$

$$\lambda^* = \frac{B^* \cdot D^* - 1}{A^* \cdot C^*},$$

$$\delta^* = \beta^{*2} - 4\lambda^*,$$

$$A^* = SoS_{pipe}^2 \left(\frac{1}{\rho_L a_L^2} - \frac{1}{\rho_g a_g^2}\right),$$

$$B^* = SoS_{pipe}^2 \left[\left(\frac{d}{t}\right)\left(\frac{1-v^2}{E}\right) + \frac{1}{\rho_g a_g^2}\right],$$

$$C^* = (\rho_L - \rho_g), \text{ and}$$

$$D^* = \rho_g$$

According to aspects of the present disclosure, unlike the WLR in the oil-and-water mixture, both roots of HL in Equation 22 are valid. The positive root represents a liquid-rich mixture, whereas the negative root represents the gas-rich mixture. This is because the curve based on Wood's equation takes a minimum value within the possible HL range (0 to 1), and thus, for some SoS values, a dual solution corresponding to positive and negative roots of HL exists.

In aspects of the present disclosure, once the inline phase fraction HL is determined, the inline phase flow rates can be calculated as shown below:

$$Q_{total} = V \cdot \text{Area}$$

$$Q_{gas} = Q_{total} \cdot (1 - HL)$$

$$Q_{liquid} = Q_{total} \cdot HL \quad (23)$$

where
Q the volumetric flow rate,
V: the fluid velocity, and
Area: the cross-sectional area of the flowmeter.

According to aspects of the present disclosure, the flow rate derivations using Equations 17 and 23 assume well-mixed flows. For the gas-and-liquid flows, it is also possible to implement various multiphase flow algorithms to consider possible slip conditions between the phases.

In aspects of the present disclosure, standard phase flow rates can be obtained by using the inline phase flow rates and the conversion factors (derived from PVT analysis of an initial fluid report) in the flowmeter's parameter file.

A detailed description of the disclosed techniques for deriving target downhole phase fractions and determining downhole flow rates is described below with reference to FIGS. 2-6, in accordance with aspects of the present disclosure. Initially, the operator typically provides a report of a bottomhole fluid sample analysis. The data in the report is fed into a pressure, volume, and temperature (PVT) software package to create an initial parameter file for the flowmeter.

Figure 2:
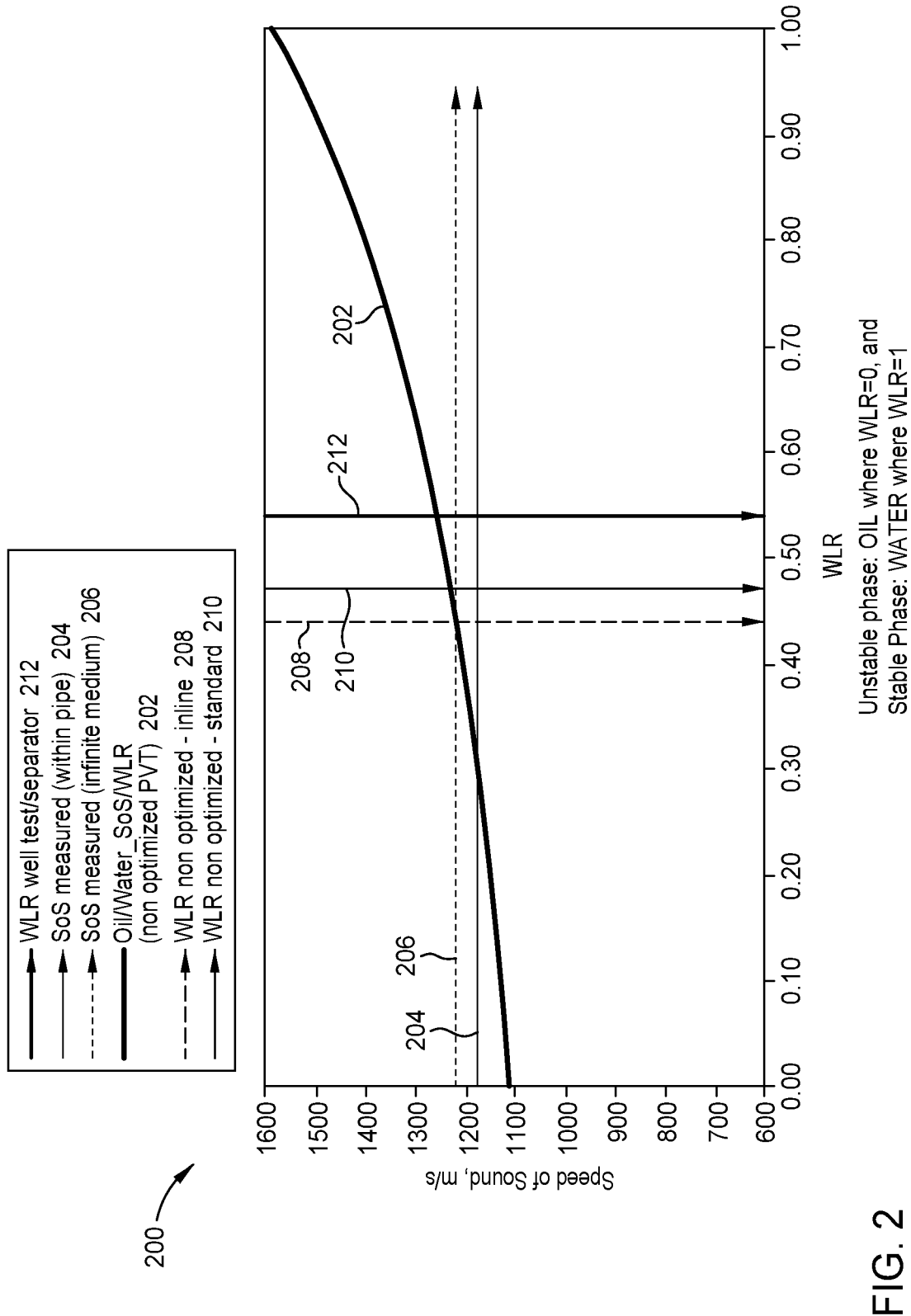
FIG. 2 is an example set of curves illustrating an example set of parameters for deriving phase fractions and volumetric flow rates for each phase component of a well, in accordance with aspects of the present disclosure.

FIG. 2 is an example set of curves 200 illustrating an example set of parameters (e.g., for inclusion in a parameter file) for deriving phase fractions and volumetric flow rates for each phase component of a well (e.g., an oil well), in accordance with certain aspects of the present disclosure. The curves may be determined utilizing the components shown in FIG. 1. Curve 202 is a SoS-$\phi_d$(t) curve showing the relationship between the SoS and the downhole phase fraction. This initial curve can be drawn once the pressure $P_d$(t) and temperature $T_d$(t) measurements are made at time t: the SoS values for each phase for the measured $P_d$(t) and $T_d$(t) are interpolated from the tabulated SoS values for a range of P and T grid values in the parameter file, and the phase fraction $\phi_d$ is systematically changed from 0 to 1 in Wood's equation (Equation 10) to obtain the corresponding mixture SoS. This is followed by plotting the SoS-$\phi_d$ pairs. The curve 202 in FIG. 2 is an example SoS-$\phi_d$(t) curve with $\phi_d$=WLR. The horizontal line 204 is a compliant SoS(t) as measured by the flowmeter (e.g., flowmeter 130) independently. The horizontal line 206 is a corresponding $SoS_{mix}$(t) for the infinite medium that is obtained using Eq. 9. The vertical line 208 is determined based on the intersection of curve 202 and line 206 and shows a value of $WLR_{inline}$(t). The vertical line 210 indicates a value of $WLR_{standard}$(t) that is calculated based on flow rates that are calculated based on measurements and the disclosed flow algorithm.

According to aspects of the present disclosure, once $WLR_{standard}$(t) is calculated, the flowmeter continues to report flow rates based on the five curves/lines 202, 204, 206, 208, and 210. Typically, this is the time frame from the installation of the flowmeter in the well to the first well test or separator test. The periodicity for well or separator tests may be determined by the operator. When the well or separator test data become available, a comparison analysis may be made to determine the phase flow rate performance of the flowmeter.

In aspects of the present disclosure, vertical line 212 (see FIG. 2) is the phase fraction determined from the well tests, which may become available later (e.g., weeks or months after installation of the flowmeter). If the discrepancy between the phase fractions from the well tests (line 212) and the flowmeter (line 210) is larger than the allowed delta (typically ≤5%), then a correction process may be run.

Figure 3:
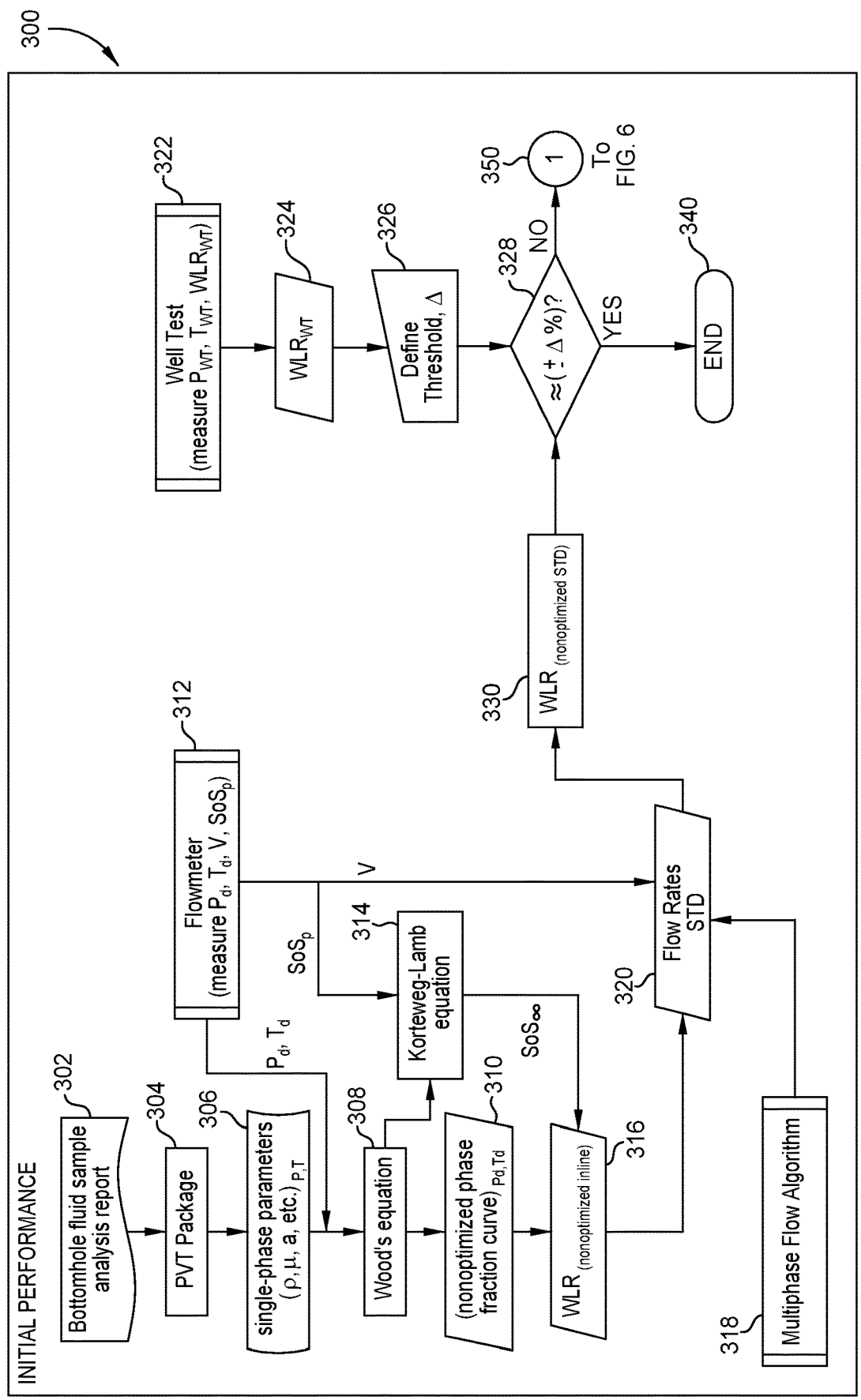
FIG. 3 illustrates example operations for an initial flowmeter measurement for a given flow condition, in accordance with aspects of the present disclosure.

FIG. 3 illustrates example operations 300 for an initial flowmeter measurement for a given flow condition, according to aspects of the present disclosure. At 302, a bottomhole fluid (e.g., a fluid mixture) sample analysis report is obtained. Data from the bottomhole fluid sample analysis report is analyzed with a PVT software package at 304 to determine single-phase parameters (e.g., density, ρ; viscosity, μ; and SoS, a) of the analyzed mixture at various pressures (P) and temperatures (T), such as the downhole, separator, and standard pressures and temperatures. The single-phase parameters are represented at 306. A flowmeter (e.g., the flowmeter 130 shown in FIG. 1) measures the downhole pressure ($P_d$), downhole temperature ($T_d$), fluid velocity (V), and SoS in the medium in the pipe ($SoS_p$, e.g., curve 204 in FIG. 2) of the fluid mixture at 312. Wood's equation (see Equation 10, above) is used with the single-phase parameters, $P_d$, and $T_d$ at 308 to determine a non-optimized phase-fraction curve (e.g., curve 202 in FIG. 2). The non-optimized phase-fraction curve is represented at 310. The $SoS_p$ determined by the flowmeter and Wood's equation are used with the Korteweg-Lamb equation (see Equation 9, above) at 314 to determine the SoS in the infinite medium ($SoS_\infty$, also referred to herein as $SoS_{mix}$, e.g., line 206 in FIG. 2). The non-optimized phase-fraction curve and the $SoS_\infty$ are used at 316 to determine a non-optimized inline WLR ($WLR_{nonoptimized\ inline}$, e.g., the line 208 in FIG. 2). The non-optimized inline WLR, fluid velocity, and a multiphase flow algorithm 318 are used at 320 to determine flow rates for the mixture at standard (STD) temperature and pressure. The flow rates for the mixture at standard temperature and pressure are used in calculating a non-optimized WLR for the mixture at standard temperature and pressure ($WLR_{nonoptimized}$ STD, e.g., the line 210 in FIG. 2) at 330. At 322, measures of pressure ($P_{WT}$), temperature ($T_{WT}$), and water-in-liquid ratio ($WLR_{WT}$, e.g., line 212 in FIG. 2) from a well test are determined. The $WLR_{WT}$ 324 is used in determining a delta threshold (Δ, e.g., 5%) at 326. At 328, the $WLR_{nonoptimized}$ STD is compared to the $WLR_{WT}$. If the difference between the $WLR_{nonoptimized\ STD}$ and the $WLR_{WT}$ is less than or equal to Δ, then the flowmeter is considered to be providing accurate measures of the downhole WLR and standard WLR, no adjustment of measurements from the flowmeter are needed, and operations 300 end at 340. If the difference between the $WLR_{nonoptimized\ STD}$ and the $WLR_{WT}$ is greater than Δ, then the flowmeter is considered as not providing accurate measures of the downhole WLR and standard WLR, and operations 300 proceed to 350.

Figure 4:
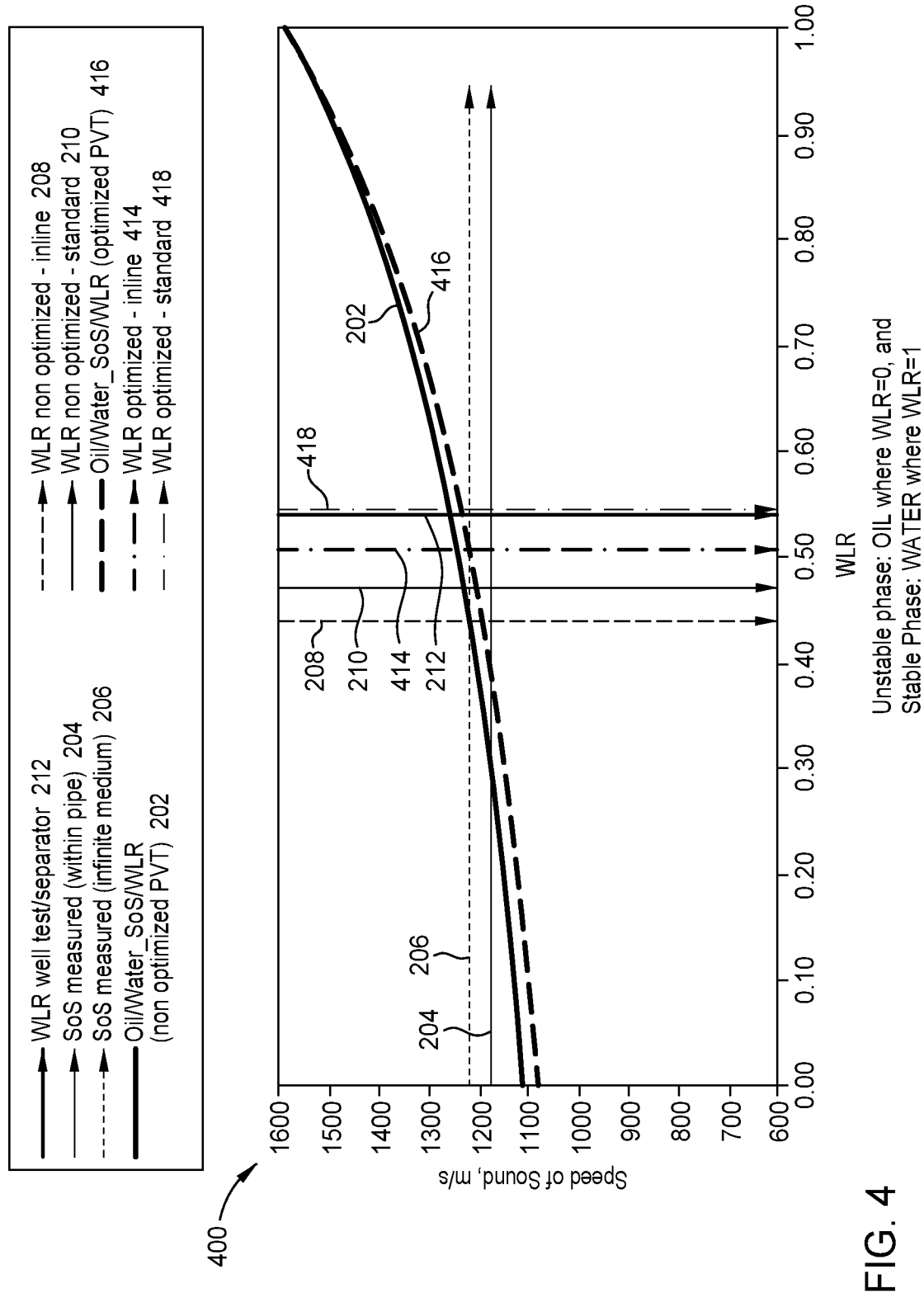
FIG. 4 is an example set of curves/lines illustrating an example set of parameters for deriving phase fractions and volumetric flow rates for each phase component while treating a water component as stable, in accordance with aspects of the present disclosure.

FIG. 4 is an example set of curves 400 illustrating an example set of parameters (e.g., for inclusion in a parameter file) for deriving phase fractions and volumetric flow rates for each phase component of a well (e.g., the same well discussed above with reference to FIG. 2), in accordance with certain aspects of the present disclosure. The curves 202, 204, 206, 208, 210, and 212 are the same curves illustrated in FIG. 2 and will not be further described. The set of curves 400 are for use in an optimization process that assumes that the unstable single-phase SoS belongs to oil. Typically, this approach is desirable when two-phase flow is expected, in which case the water phase can be chosen as the stable phase due to the incompressibility of the water. In some situations, however, it is possible that the initial fluid coming out of the well is dry oil (i.e., 100% oil). For those cases, the single-phase SoS for oil is based on an accurate direct measurement of the flowmeter. It may then be desirable to treat the oil phase as the stable phase, while the production water can be selected as the unstable phase. This is discussed below with reference to FIG. 5. In FIG. 4, curve 414 is a derived inline phase fraction. The derivation is based on the phase fraction ratio of the flowmeter ($\phi_{inline}/\phi_{std}$), standard phase fraction of the flowmeter ($\phi_{std}$), phase fraction of well/separator tests ($\phi_{WT}$), downhole pressure and temperature measurements ($P_d$, $T_d$), well/separator test pressure and temperature measurements ($P_{WT}$, $T_{WT}$), and the standard pressure and temperature ($P_{std}$, $T_{std}$) conditions. Example techniques of the derivation of inline phase fractions are described above with reference to Equations 5 and 7. Using this derived phase fraction, a mixture density ($\rho_{mix}$) and a corresponding mixture speed of sound ($SoS_{mix}$) are calculated using Equations 8 and 9, respectively. Curve 416 is a derived SoS-$\phi_d$(t) curve showing the relationship between the adjusted SoS and the downhole phase fraction. The derived SoS-$\phi_d$(t) curve is obtained by changing the single-phase SoS value of the unstable phase in Equation 10 and making use of the known and predicted parameters. Derivation of the curve 416 may be followed by updating the single-phase SoS values in the parameter file at the measured $P_d$ and $T_d$ values and then extrapolating the updates to other values of P and T in the parameter file. Once the parameter file is updated, the flowmeter measurements may be used to obtain the standard phase flow rates. Line 418 is the derived standard phase fraction, $\phi_{std}$, which may be obtained by using the standard flow rates reported by the flowmeter.

Figure 5:
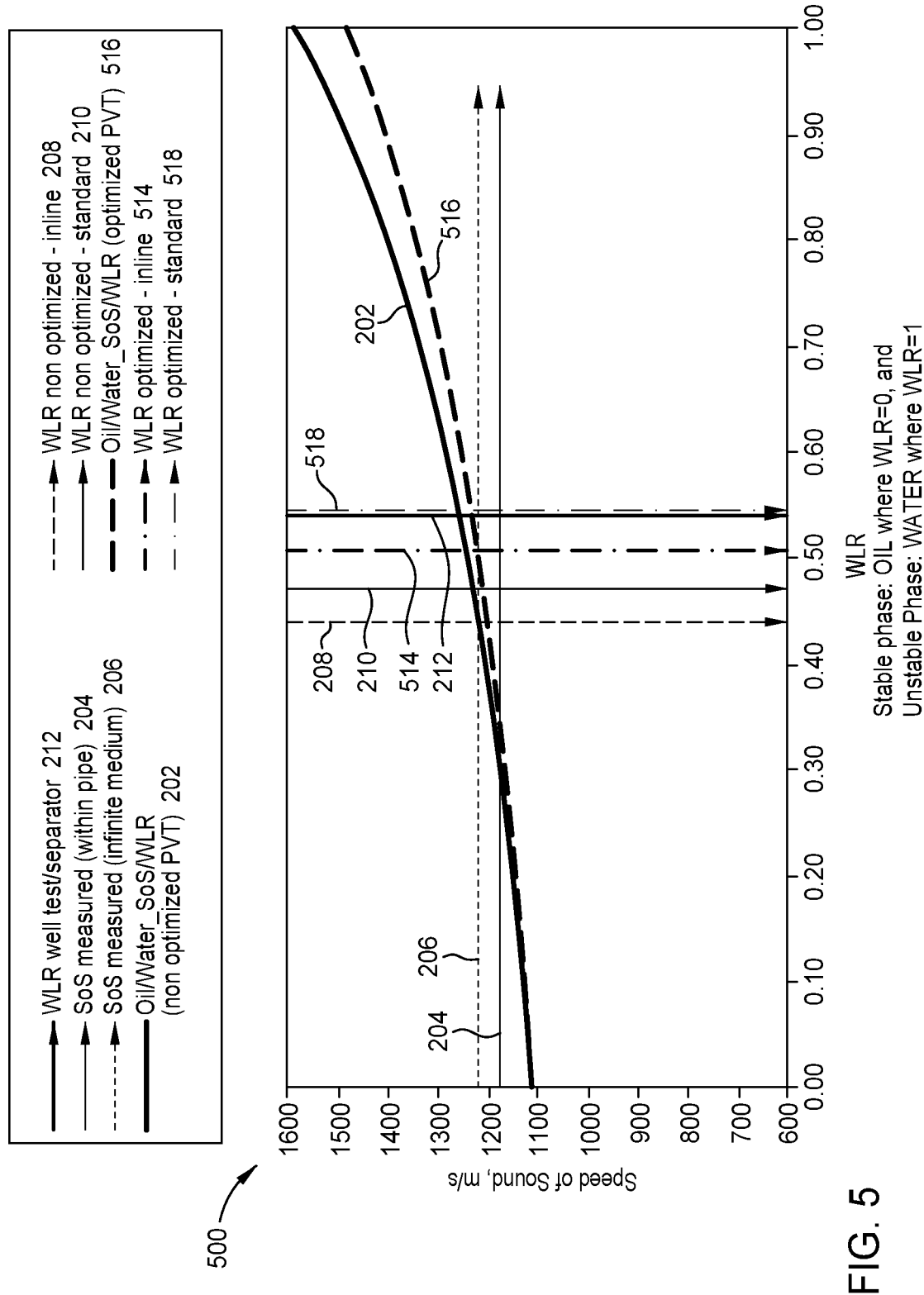
FIG. 5 is an example set of curves/lines illustrating an example set of parameters for deriving phase fractions and volumetric flow rates for each phase component while treating an oil component as stable, in accordance with aspects of the present disclosure.

FIG. 5 is an example set of curves 500 illustrating an example set of parameters (e.g., for inclusion in a parameter file) for deriving phase fractions and volumetric flow rates for each phase component of a well (e.g., the same well discussed above with reference to FIGS. 2 and 4), in accordance with certain aspects of the present disclosure. The curves 202, 204, 206, 208, 210, and 212 are the same curves illustrated in FIGS. 2 and 4 and will not be further described. The set of curves 500 are for use in an optimization process that assumes that the unstable single-phase SoS belongs to water. Typically, this approach is desirable when the initial fluid coming out of the well is dry oil (i.e., 100% oil). The single-phase SoS for oil may be based on an accurate direct measurement of the flowmeter. It may be desirable to treat the oil phase as the stable phase, while the production water can be selected as the unstable phase. In FIG. 5, line 514 is a derived inline phase fraction. The derivation is based on the phase fraction ratio of the flowmeter ($\phi_{inline}/\phi_{std}$), standard phase fraction of the flowmeter ($\phi_{std}$), phase fraction of well/separator tests ($\phi_{WT}$), downhole pressure and temperature measurements ($P_d$, $T_d$), well/separator test pressure and temperature measurements ($P_{WT}$, $T_{WT}$), and the standard pressure and temperature ($P_{std}$, $T_{std}$) conditions. Using this derived phase fraction, a mixture density ($\rho_{mix}$) and a corresponding mixture speed of sound ($SoS_{mix}$) are calculated using Equations 8 and 9, respectively. Curve 516 is a derived SoS-$\phi_d$(t) curve showing the relationship between the adjusted SoS and the downhole phase fraction. The derived SoS-$\phi_d$(t) curve is obtained by changing the single-phase SoS value of the unstable phase in Equation 10 and making use of the known and predicted parameters. Derivation of the curve 516 may be followed by updating the single-phase SoS values in the parameter file at the measured $P_d$ and $T_d$ values and then extrapolating the updates to other values of P and T in the parameter file. Once the parameter file is updated, the flowmeter measurements may be used to obtain the standard phase flow rates. Line 518 is the derived standard phase fraction, $\phi_{std}$, which may be obtained by using the standard flow rates reported by the flowmeter.

Figure 6:
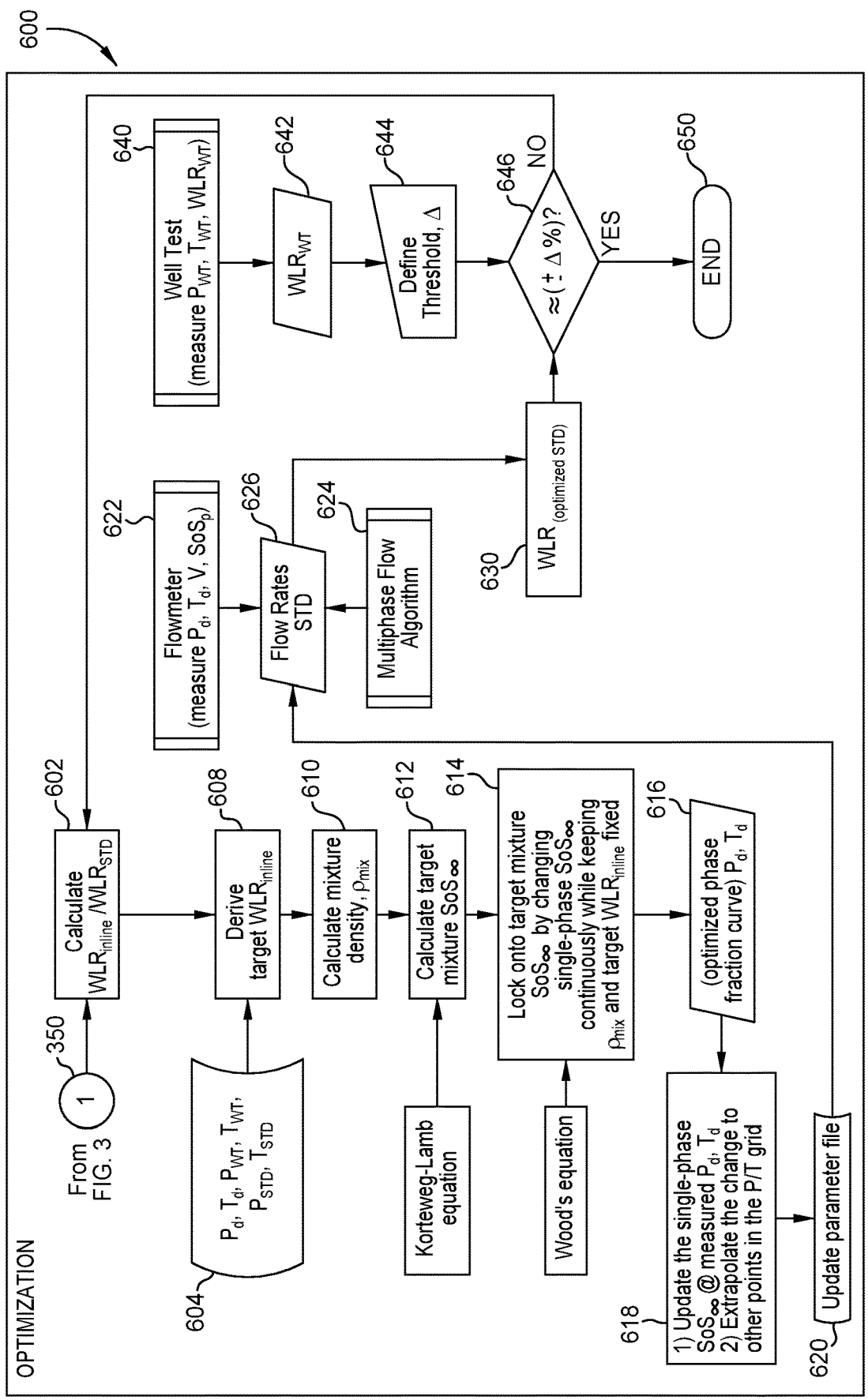
FIG. 6 illustrates example operations for adjusting parameters for a flowmeter for a given flow condition, in accordance with aspects of the present disclosure.

FIG. 6 illustrates example operations 600 for adjusting parameters for a flowmeter for a given flow condition, according to aspects of the present disclosure. The operations 600 may follow after the operations 300 (see FIG. 3) if the difference between the $WLR_{nonoptimized\ STD}$ and the $WLR_{WT}$ is greater than Δ, as symbolized by operations 600 beginning at 350 (see FIG. 3). At 602, the ratio $WLR_{inline}/$ $WLR_{STD}$ is calculated. Data from the well test (e.g., $P_{WT}$, $T_{WT}$) and from the flowmeter (e.g., $P_d$, $T_d$) at 604 is used with $P_{std}$ and $T_{std}$ at 608 to derive a target adjusted ratio $WLR_{inline}$ (e.g., curve 414 in FIG. 4 or curve 514 in FIG. 5) as was demonstrated in Equations 5 and 7. At 610, a mixture density ($\rho_{mix}$) is calculated based on the target adjusted ratio $WLR_{inline}$. The Korteweg-Lamb equation (see Equation 9, above) is used to calculate the target mixture SoS in the infinite medium ($SoS_\infty$) at 612. The target mixture $SoS_\infty$, $\rho_{mix}$, and $WLR_{inline}$ are used with Wood's equation (see Equation 10, above) to determine the single-phase $SoS_\infty$ for the unstable phase at 614. The optimized phase fraction curve is determined at 616 by adjusting the non-optimized phase fraction curve based on the determined $SoS_\infty$ for the unstable phase. At 618, the $SoS_\infty$ for the unstable phase at the measured downhole pressure ($P_d$) and downhole temperature ($T_d$) is updated to the value determined at 614. The change to the $SoS_\infty$ for the unstable phase is also extrapolated to other pressures and temperatures at 618. The parameter file for the flowmeter is updated based on the $SoS_\infty$ for the unstable phase at 620. The updated parameters and measurements 622 of $P_d$, $T_d$, fluid velocity, and SoS in the pipe are used with a multiphase flow algorithm 624 at 626 to determine flow rates for the mixture at standard (STD) temperature and pressure. The flow rates for the mixture at standard temperature and pressure are used in calculating an optimized WLR for the mixture at standard temperature and pressure ($WLR_{optimized\ STD}$, e.g., line 418 in FIG. 4 or line 518 in FIG. 5) at 630. At 640, measures of pressure ($P_{WT}$), temperature ($T_{WT}$), and water-in-liquid ratio ($WLR_{WT}$, e.g., line 212 in FIG. 2) from a well test are determined. A delta threshold ($\Delta$, e.g., 5%) based on the user specifications is defined independently at 644. At 646, the $WLR_{optimized}$ STD is compared to the $WLR_{WT}$. If the difference between the $WLR_{optimized}$ STD and the $WLR_{WT}$ is less than or equal to $\Delta$, then the flowmeter is considered to be providing accurate measures of the downhole WLR and standard WLR, no additional adjustment of measurements from the flowmeter are needed, and operations 600 end at 650. If the difference between the $WLR_{optimized}$ STD and the $WLR_{WT}$ is greater than $\Delta$, then the flowmeter is considered to not be providing accurate measurements of the downhole WLR and standard WLR, and operations 600 return to 350.

Figure 7:
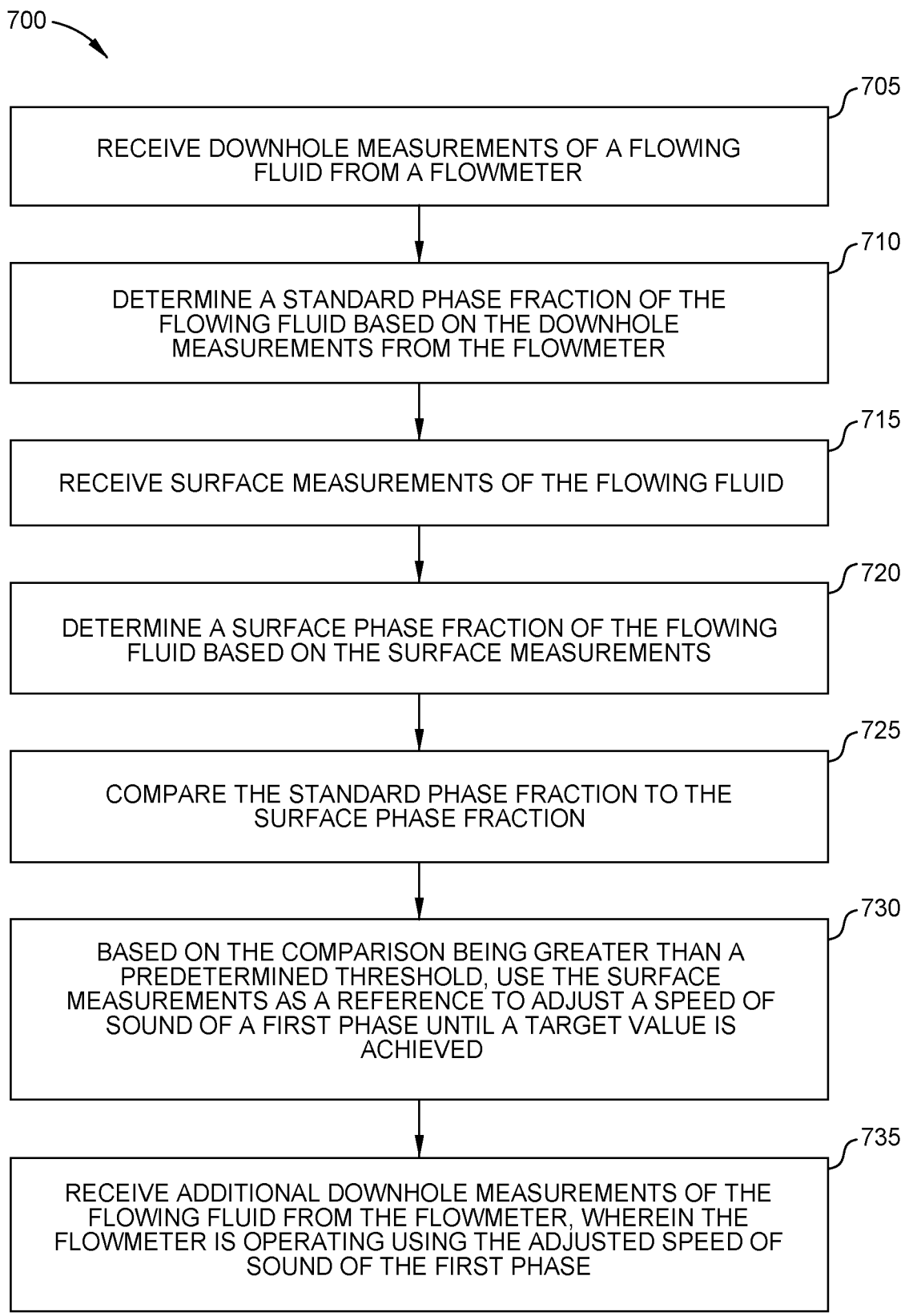
FIG. 7 illustrates example operations for hydrocarbon monitoring, in accordance with aspects of the present disclosure.

FIG. 7 illustrates example operations 700 for hydrocarbon monitoring, in accordance with aspects of the present disclosure. Operations 700 may be performed by or using the flowmeter 130 illustrated in FIG. 1, a processing system, and/or other components of a system for performing hydrocarbon monitoring.

Operations 700 begin at block 705 by receiving downhole measurements of a flowing fluid from a flowmeter. For example, processor 112 (see FIG. 1) may receive measurements of downhole pressure ($P_d$), downhole temperature ($T_d$), fluid velocity (V), and SoS of the fluid 110 in the conduit 105 ($SoS_p$) from the flowmeter 130.

At block 710, operations 700 continue by determining a standard phase fraction of the flowing fluid based on the downhole measurements from the flowmeter. Continuing the example from above, the processor 112 may determine a water-in-liquid ratio for standard conditions ($WLR_{STD}$) of the flowing fluid 110 based on the $P_d$, $T_d$, V, and $SoS_p$ received from the flowmeter 130 at block 705. In the example, the processor may determine $WLR_{STD}$ using the techniques described above with reference to FIG. 2.

Operations 700 continue at block 715 by receiving surface measurements of the flowing fluid. Continuing the example, the processor may receive measurements from sensors at the separator 160 of pressure ($P_{sep}$) and temperature ($T_{sep}$) of the flowing fluid 110.

At block 720, operations 700 continue by determining a surface phase fraction of the flowing fluid based on the surface measurements. Continuing the example from above, the processor 112 may determine a water-in-liquid ratio at the separator ($WLR_{sep}$) based on the $P_{sep}$ and $T_{sep}$ received at block 715.

Operations 700 continue at block 725 by comparing the standard phase fraction to the surface phase fraction. Continuing the above example, the processor 112 may compare the $WLR_{STD}$ from block 710 with the $WLR_{sep}$ from block 720.

At block 730, operations 700 continue by using the surface measurements as a reference to adjust a SoS of a first phase until a target value is achieved, based on the comparison being greater than a predetermined threshold. Continuing the example from above, the processor, based on the comparison from block 725 being greater than a predetermined threshold ($\Delta$), may use the $T_{sep}$, $P_{sep}$, and surface phase fraction from block 720 as a reference to derive an inline target phase fraction, an inline target mixture density, an inline target $SoS_{mix}$ by utilizing the SoS measured at block 705, and adjust a SoS of a first phase ($SoS_1$), e.g., an oil phase, until a SoS of the fluid mixture ($SoS_{mix}$) matches the target $SoS_{mix}$.

Operations 700 continue at block 735 by receiving additional downhole measurements of the flowing fluid from the flowmeter, wherein the flowmeter is operating using the adjusted SoS of the first phase. Continuing the example from above, the processor 112 may receive additional measurements of $P_d$, $T_d$, V, and $SoS_p$), where the flowmeter 130 may use the adjusted $SoS_1$ from block 730 in making the additional measurements.

According to aspects of the present disclosure, a device or system performing operations 700 may determine at least one of an updated in-situ phase fraction, an updated standard phase fraction, or updated phase flow rates of the flowing fluid, based on the additional downhole measurements of block 735.

In aspects of the present disclosure, the standard phase fraction of block 710 may include a water-in-liquid ratio (WLR) at standard conditions.

According to aspects of the present disclosure, the surface measurements of the flowing fluid of block 715 may be received from at least one of a wellhead (e.g., wellhead 150, see FIG. 1) or a separator (e.g., separator 160, see FIG. 1).

In aspects of the present disclosure, the target value of block 730 may include a target mixture SoS ($SoS_{mix}$). In some such aspects, using the surface measurements as the reference to adjust the SoS of the first phase as in block 730 may include: calculating a target mixture density based on the surface phase fraction; calculating the target mixture SoS based on the target mixture density; and changing the SoS of the first phase until a resulting mixture SoS obtained from the Wood's equation is within a predetermined deviation from the target mixture SoS, while leaving a SoS of a second phase constant. In some other such aspects, the SoS of the first phase is a SoS of oil and the SoS of the second phase is a SoS of water. In some other such aspects, the SoS of the first phase is a SoS of gases in the fluid, the SoS of the second phase is a SoS of liquids in the fluid, and the phase fraction comprises a liquid volume fraction (HL) of the fluid. In some other such aspects, calculating the target mixture density may include: predicting an in-situ phase fraction based on the surface phase fraction, the standard phase fraction, a downhole pressure measurement, a downhole temperature measurement, a surface pressure measurement, a surface temperature measurement, a standard pressure, and a standard temperature; and calculating the target mixture density based on the in-situ phase fraction. In still other such aspects, calculating the target mixture SoS may be based on the Korteweg-Lamb equation.

According to aspects of the present disclosure, a device or system performing operations 700 may update a parameter file for the flowmeter with the adjusted SoS of the first phase of block 730. In some such aspects, the adjusted SoS of the first phase is at a measured downhole temperature and a measured downhole pressure and the updating may include: extrapolating additional adjusted speeds of sound of the first phase for temperatures other than the measured downhole temperature and for pressures other than the measured downhole pressure; and writing the adjusted SoS of the first phase at the measured downhole temperature and pressure and the extrapolated additional adjusted speeds of sound of the first phase to the parameter file for the flowmeter.

In aspects of the present disclosure, a device or system performing operations 700 may apply a conversion factor to at least one of the standard phase fraction of block 710 or the surface phase fraction of block 720 before the comparing of block 725.

According to aspects of the present disclosure, the flowmeter of block 705 may include an optical flowmeter or an electrical flowmeter.

In aspects of the present disclosure, a device or system performing operations 700 may determine an updated standard phase fraction of the flowing fluid based on the additional downhole measurements of block 735; receive additional surface measurements of the flowing fluid; determine an updated surface phase fraction of the flowing fluid based on the additional surface measurements; compare the updated standard phase fraction to the updated surface phase fraction; based on the comparison of the updated standard and surface phase fractions being greater than the predetermined threshold, use the additional surface measurements as an updated reference to alter the SoS of the first phase until an updated target value is achieved; and receive further downhole measurements of the flowing fluid from the flowmeter, wherein the flowmeter operates using the altered SoS of the first phase. In some such aspects of the present disclosure, a device or system performing operations 700 may calculate adjustments to past downhole measurements (e.g., a database of historical downhole measurements gathered by the flowmeter before operations 700 begin) based on the altered SoS of the first phase.

In aspects of the present disclosure, a device or system performing operations 700 may calculate adjustments to past downhole measurements (e.g., a database of historical downhole measurements gathered by the flowmeter before operations 700 begin) based on the adjusted SoS of the first phase.

Aspects and Advantages of Flow Rate Optimizer

The challenges associated with in-well multiphase flow measurement are numerous. Consequently, there are not many technologies available for this challenging task. One approach that has been used is a Venturi-based solution in which the Venturi is combined with other technologies. However, it is well-known that Venturi-based solutions have some fundamental issues in a downhole, multiphase environment. First, the Venturi-based solution is not full-bore, and the primary design causes significant pressure loss due to the restriction of the flow. This restriction may also prevent some well operations, and as a result, this may not be a preferred solution by operators. Second, the Venturi meters have limited flow rate ranges due to their low turndown ratios. Third, Venturi meters are suitable for single-phase flows and do not provide phase fraction measurements, such as water cut. Fourth, most Venturi-based solutions are based on electronic technology, which may not be suitable for severe in-well conditions. The lifetimes of electronic gauges, as well as the drift in their measurements, are also some of the primary reasons that these meters are not frequently used.

There is, however, an increasing trend in designing "intelligent completions" in which the well is equipped with in-flow control valves (ICVs) or in-flow control devices (ICDs) so that the well production may be optimized (or at least so that well production efficiency may be increased) by creating an even flow distribution, particularly for multi-zone applications. To achieve this, the flow in the well may be measured for the life of the well. It is clear that there is a gap between what is expected from in-well flow measurement and what is currently offered. Aspects of the present disclosure may close this gap and provide significant advantages over existing flow measurement solutions. Some of these advantages are listed below.

Eliminate Reliance on New Bottomhole Samples and Reservoir Analysis:

The composition of the reservoir fluids is important for any type of flowmeter. The flowmeter described herein also uses a parameter file that consists of fluid properties including density, viscosity, SoS, and formation volume factor of the individual phases that form the fluid mixture. These values are typically based on the analysis of bottomhole samples. The flowmeter then takes the parameter file and combines the values in the file with the flowmeter's own measurements to interpret the downhole and standard phase flow rates. As a result, depending on the accuracy of the data obtained from bottomhole fluid samples, the phase flow rates are impacted. The most difficult parameter to measure, which is also closely related to other parameters in a given application, is the single-phase SoS. Naturally, as the composition of the fluids produced from a well may change over time, it is expected that a new parameter file may be created in response to the changes in the fluid composition, particularly for the SoS of the single phases. In aspects of the present disclosure, new parameter files need not be created, as aspects of the present disclosure update the used parameter files based on test results and ongoing operations.

No Intervention of Well Operations:

Because it is not necessary to obtain additional bottom hole fluid samples in later periods of operation of the well when using aspects of the present disclosure, intervening in well operations to improve the accuracy of those aspects is significantly reduced. This may result in reduced losses in production time, as compared to previously known techniques.

Better Economics:

Even if the above-described production losses are excluded, the cost of obtaining bottomhole fluid samples by the operator, performing reservoir analysis and preparing the reports on those bottomhole samples by a third party, and creating flowmeter (e.g., optical flowmeter (OFM)) parameter files using PVT software packages may result in very large expenses when combined. Aspects of the present disclosure may reduce many or all of these costly and lengthy activities.

Fast Turnaround Time:

Once the well test data and corresponding flowmeter (e.g., OFM) measurements are available, the implementation of aspects of the present disclosure may be fast (e.g., 1 day).

Better Accuracy and Performance:

In aspects of the present disclosure, the flowmeter velocity and SoS measurements, as well as the pressure and temperature measurements, are independent of the composition of the fluid. Thus, there is no change in the accuracy of the flowmeter measurements due to changes of the composition of the fluid. However, because aspects of the present disclosure use the well test results as a reference to back-calculate and determine the sound speed of the unstable phase, the result may be a high-performance measurement. In contrast, this sort of performance increase is not expected from an actual bottomhole sample analysis. Potential errors in sampling activities used in other techniques include sampling production from a different zone, insufficient flow rate or "heading," loss of liquid or solids due to drawdown, a compositional gradient in the reservoir, poor cleanup of drilling or workover fluids, loss of gas due to drawdown, gas coning, loss of reactive components to tubing, release of contaminants from the tubing, transfer of a nonhomogeneous sample, separator instability, liquid carry-over from the separator, emulsions or gas carry-under from the separator, flow-rate errors, poor sampling practices, and errors in data recording. These potential errors can all mean that samples may not be fully representative of the reservoir fluid. Furthermore, good fluid samples may also be studied under invalid conditions. Aside from the P and T errors that can influence measurements, the errors in gas/oil ratio (GOR) may have a major influence on a PVT study.

Independent of Sensor Type:

Although aspects of the present disclosure have been described using an optical flowmeter as an example, the implementation of the disclosed aspects is independent of the sensor type, and thus can be applied to electronic-based sensors, as long as the sensors measure SoS.

CONCLUSION

Certain aspects of the present disclosure provide a flow algorithm based on SoS measurements of the fluid mixture and single-phase SoS optimizations. The algorithm uses well test results as a reference to back-calculate and determine the SoS of the unstable phase.

Any of the operations described above, such as the operations 700 of FIG. 7, may be included as instructions in a computer-readable medium for execution by a processor (e.g., processor 112 of FIG. 1) or any other suitable processing system. The computer-readable medium may comprise any suitable memory for storing instructions, such as read-only memory (ROM), random access memory (RAM), flash memory, an electrically erasable programmable ROM (EEPROM), a compact disc ROM (CD-ROM), or a floppy disk.

While the foregoing is directed to aspects of the present disclosure, other and further aspects may be devised without departing from the basic scope thereof, and the scope thereof is determined by the claims that follow.

The invention claimed is:

1. A method of hydrocarbon monitoring, comprising:
receiving downhole measurements of a flowing fluid from a flowmeter;
determining a standard phase fraction and a speed of sound (SoS) of a first phase of the flowing fluid based on the downhole measurements from the flowmeter;
receiving surface measurements of the flowing fluid;
determining a surface phase fraction of the flowing fluid based on the surface measurements;
comparing the standard phase fraction to the surface phase fraction to generate a comparison;
adjusting, based on the comparison being greater than a predetermined threshold and using the surface measurements as a reference, the SoS of the first phase until a target value is achieved, to generate an adjusted SoS of the first phase; and
receiving additional downhole measurements of the flowing fluid from the flowmeter, wherein the flowmeter is operating using the adjusted SoS of the first phase for the additional downhole measurements.

2. The method of claim 1, further comprising determining at least one of an updated in-situ phase fraction, an updated standard phase fraction, or updated phase flow rates of the flowing fluid, based on the additional downhole measurements.

3. The method of claim 1, wherein the standard phase fraction comprises a water-in-liquid ratio (WLR) at standard conditions.

4. The method of claim 1, wherein the surface measurements of the flowing fluid are received from at least one of a wellhead or a separator.

5. The method of claim 1, wherein the target value comprises a target mixture SoS.

6. The method of claim 5, wherein using the surface measurements as the reference to adjust the SoS of the first phase comprises:
calculating a target mixture density based on the surface phase fraction;
calculating the target mixture SoS based on the target mixture density; and
changing the SoS of the first phase until a resulting mixture SoS obtained from the Wood's equation is within a predetermined deviation from the target mixture SoS, while leaving a SoS of a second phase constant.

7. The method of claim 6, wherein the SoS of the first phase is a SoS of oil and wherein the SoS of the second phase is a SoS of water.

8. The method of claim 6, wherein the SoS of the first phase is a SoS of gases in the fluid, wherein the SoS of the second phase is a SoS of liquids in the fluid, and wherein the phase fraction comprises a liquid volume fraction (HL) of the fluid.

9. The method of claim 6, wherein calculating the target mixture density comprises:
predicting an in-situ phase fraction based on the surface phase fraction, the standard phase fraction, a downhole pressure measurement, a downhole temperature measurement, a surface pressure measurement, a surface temperature measurement, a standard pressure, and a standard temperature; and
calculating the target mixture density based on the in-situ phase fraction.

10. The method of claim 6, wherein calculating the target mixture SoS is based on the Korteweg-Lamb equation.

11. The method of claim 1, further comprising updating a parameter file for the flowmeter with the adjusted SoS of the first phase.

12. The method of claim 11, wherein the adjusted SoS of the first phase is at a measured downhole temperature and a measured downhole pressure and wherein the updating comprises:

extrapolating additional adjusted speeds of sound of the first phase for temperatures other than the measured downhole temperature and for pressures other than the measured downhole pressure; and writing the adjusted SoS of the first phase at the measured downhole temperature and pressure and the extrapolated additional adjusted speeds of sound of the first phase to the parameter file for the flowmeter.

13. The method of claim 1, further comprising applying a conversion factor to at least one of the standard phase fraction or the surface phase fraction before the comparing.

14. The method of claim 1, wherein the flowmeter comprises an optical flowmeter.

15. The method of claim 1, further comprising:
determining an updated standard phase fraction of the flowing fluid based on the additional downhole measurements;
receiving additional surface measurements of the flowing fluid;
determining an updated surface phase fraction of the flowing fluid based on the additional surface measurements;
comparing the updated standard phase fraction to the updated surface phase fraction to generate a comparison of the updated standard and surface phase fractions;
altering, based on the comparison of the updated standard and surface phase fractions being greater than the predetermined threshold and using the additional surface measurements as an updated reference, the adjusted SoS of the first phase until an updated target value is achieved, to generate an altered SoS of the first phase; and
receiving further downhole measurements of the flowing fluid from the flowmeter, wherein the flowmeter is operating using the altered SoS of the first phase for the further downhole measurements.

16. The method of claim 15, further comprising calculating adjustments to past downhole measurements based on the altered SoS of the first phase.

17. The method of claim 1, further comprising calculating adjustments to past downhole measurements based on the adjusted SoS of the first phase.

18. A processing system for hydrocarbon monitoring, the processing system being configured to:
receive downhole measurements of a flowing fluid from a flowmeter;
determine a standard phase fraction and a speed of sound (SoS) of a first phase of the flowing fluid based on the downhole measurements from the flowmeter;
receive surface measurements of the flowing fluid;
determine a surface phase fraction of the flowing fluid based on the surface measurements;
compare the standard phase fraction to the surface phase fraction to generate a comparison;
adjust, based on the comparison being greater than a predetermined threshold and using the surface measurements as a reference, the SoS of the first phase until a target value is achieved, to generate an adjusted SoS of the first phase; and
receive additional downhole measurements of the flowing fluid from the flowmeter, the flowmeter being configured to operate using the adjusted SoS of the first phase for the additional downhole measurements.

19. The processing system of claim 18, wherein the processing system is further configured to determine at least one of an updated in-situ phase fraction, an updated standard phase fraction, or updated phase flow rates of the flowing fluid, based on the additional downhole measurements.

20. The processing system of claim 18, wherein the standard phase fraction comprises a water-in-liquid ratio (WLR) at standard conditions.

21. The processing system of claim 18, wherein the processing system is configured to receive the surface measurements of the flowing fluid from at least one of a wellhead or a separator.

22. The processing system of claim 18, wherein the target value comprises a target mixture SoS.

23. The processing system of claim 22, wherein the processing system is configured to use the surface measurements as the reference to adjust the SoS of the first phase by:
calculating a target mixture density based on the surface phase fraction;
calculating the target mixture SoS based on the target mixture density; and
changing the SoS of the first phase until a resulting mixture SoS obtained from the Wood's equation is within a predetermined deviation from the target mixture SoS, while leaving a SoS of a second phase constant.

24. The processing system of claim 18, wherein the processing system is further configured to update a parameter file for the flowmeter with the adjusted SoS of the first phase.

25. The processing system of claim 18, wherein the processing system is further configured to apply a conversion factor to at least one of the standard phase fraction or the surface phase fraction before the comparing.

26. The processing system of claim 18, wherein the flowmeter comprises an optical flowmeter.

27. The processing system of claim 18, wherein the processing system is further configured to:
determine an updated standard phase fraction of the flowing fluid based on the additional downhole measurements;
receive additional surface measurements of the flowing fluid;
determine an updated surface phase fraction of the flowing fluid based on the additional surface measurements;
compare the updated standard phase fraction to the updated surface phase fraction to generate a comparison of the updated standard and surface phase fractions;
alter, based on the comparison of the updated standard and surface phase fractions being greater than the predetermined threshold and using the additional surface measurements as an updated reference, the adjusted SoS of the first phase until an updated target value is achieved, to generate an altered SoS of the first phase; and
receive further downhole measurements of the flowing fluid from the flowmeter, the flowmeter being configured to operate using the altered SoS of the first phase for the further downhole measurements.

28. The processing system of claim 27, wherein the processing system is further configured to calculate adjustments to past downhole measurements based on the altered SoS of the first phase.

29. The processing system of claim 18, wherein the processing system is further configured to calculate adjustments to past downhole measurements based on the adjusted SoS of the first phase.

30. A non-transitory computer-readable medium comprising instructions executable by a processing system to perform operations for hydrocarbon monitoring, the operations comprising:
- receiving downhole measurements of a flowing fluid from a flowmeter;
- determining a standard phase fraction and a speed of sound (SoS) of a phase of the flowing fluid based on the downhole measurements from the flowmeter;
- receiving surface measurements of the flowing fluid;
- determining a surface phase fraction of the flowing fluid based on the surface measurements;
- comparing the standard phase fraction to the surface phase fraction to generate a comparison;
- adjusting, based on the comparison being greater than a predetermined threshold and using the surface measurements as a reference, the SoS of the phase until a target value is achieved, to generate an adjusted SoS of the phase; and
- receiving additional downhole measurements of the flowing fluid from the flowmeter, wherein the flowmeter is operating using the adjusted SoS of the phase for the additional downhole measurements.

* * * * *